United States Patent
Pai et al.

(10) Patent No.: US 10,361,004 B2
(45) Date of Patent: Jul. 23, 2019

(54) METHOD FOR OBTAINING SKIN CARE INFORMATION, METHOD FOR SHARING SKIN CARE INFORMATION, AND ELECTRONIC APPARATUS THEREFOR

(71) Applicant: Cal-Comp Electronics & Communications Company Limited, New Taipei (TW)

(72) Inventors: Nai-Chiang Pai, New Taipei (TW); Sue-Chau Chen, New Taipei (TW); Shyh-Yong Shen, New Taipei (TW)

(73) Assignee: Cal-Comp Electronics & Communications Company Limited, New Taipei (TW)

( * ) Notice: Subject to any disclaimer, the term of this patent is extended or adjusted under 35 U.S.C. 154(b) by 6 days.

(21) Appl. No.: 15/220,399

(22) Filed: Jul. 27, 2016

(65) Prior Publication Data
US 2017/0345144 A1    Nov. 30, 2017

(30) Foreign Application Priority Data
May 24, 2016 (TW) .............................. 105116064 A

(51) Int. Cl.
*G06K 9/00* (2006.01)
*G16H 50/70* (2018.01)
(Continued)

(52) U.S. Cl.
CPC ............ *G16H 50/70* (2018.01); *A61B 5/0077* (2013.01); *A61B 5/444* (2013.01); *A61B 5/445* (2013.01);
(Continued)

(58) Field of Classification Search
None
See application file for complete search history.

(56) References Cited

U.S. PATENT DOCUMENTS

| | | | | |
|---|---|---|---|---|
| 2,097,952 | A * | 11/1937 | Lohr | A61H 35/008 |
| | | | | 15/4 |
| 2003/0065523 | A1* | 4/2003 | Pruche | A45D 44/005 |
| | | | | 382/118 |

(Continued)

FOREIGN PATENT DOCUMENTS

| EP | 1875863 | 1/2008 |
|---|---|---|
| EP | 2389573 | 11/2011 |

OTHER PUBLICATIONS

"Office Action of Europe Counterpart Application," dated Jun. 6, 2017, p. 1-p. 9, in which the listed references were cited.

*Primary Examiner* — Samah A Beg
(74) *Attorney, Agent, or Firm* — JCIPRNET

(57) ABSTRACT

A method for obtaining care information, a method for sharing care information, and an electronic apparatus therefor are provided. The method for obtaining care information includes following steps: obtaining face data of a current user from an image capturing equipment and obtaining initial skin information of the face data. classifying the current user into one of a plurality of groups according to the initial skin information by a cloud database; setting a predetermined time period and a skin-condition goal by the electronic apparatus; and obtaining a skin-achievement history of an another user in the group containing the current user according to the initial skin information, the predetermined time period and the skin-condition goal by the electronic apparatus. The skin-achievement history is care information regarding the skin-condition goal achieved by the another user under circumstances of the approximate initial skin information and the approximate predetermined time period.

14 Claims, 4 Drawing Sheets

(51) Int. Cl.
| | |
|---|---|
| *G06F 19/00* | (2018.01) |
| *A61B 5/00* | (2006.01) |
| *G06F 3/0488* | (2013.01) |
| *G06K 9/62* | (2006.01) |
| *G06T 7/00* | (2017.01) |
| *H04L 29/08* | (2006.01) |
| *G16H 30/40* | (2018.01) |
| *G16H 40/63* | (2018.01) |
| *G16H 40/67* | (2018.01) |
| *G16H 10/60* | (2018.01) |
| *G16H 50/20* | (2018.01) |

(52) U.S. Cl.
CPC .......... *G06F 3/0488* (2013.01); *G06F 19/321* (2013.01); *G06K 9/00228* (2013.01); *G06K 9/6202* (2013.01); *G06T 7/0012* (2013.01); *G16H 10/60* (2018.01); *G16H 30/40* (2018.01); *G16H 40/63* (2018.01); *G16H 40/67* (2018.01); *G16H 50/20* (2018.01); *H04L 67/10* (2013.01); *G06T 2207/30088* (2013.01)

(56) References Cited

U.S. PATENT DOCUMENTS

| | | | | |
|---|---|---|---|---|
| 2003/0065588 | A1* | 4/2003 | Rubinstenn | A45D 44/005 705/26.41 |
| 2006/0010010 | A1* | 1/2006 | Wiegand | A61B 5/0059 705/2 |
| 2008/0119913 | A1* | 5/2008 | Powell | A61N 5/0616 607/88 |
| 2008/0161661 | A1* | 7/2008 | Gizewski | A61B 5/0059 600/306 |
| 2009/0043293 | A1* | 2/2009 | Pankratov | A61B 18/203 606/9 |
| 2009/0137908 | A1* | 5/2009 | Patwardhan | A61B 5/0059 600/476 |
| 2009/0182594 | A1* | 7/2009 | Choubey | G06Q 10/06 705/7.33 |
| 2009/0299154 | A1* | 12/2009 | Segman | A61B 5/0059 600/301 |
| 2010/0185064 | A1* | 7/2010 | Bandic | A61B 5/0059 600/306 |
| 2012/0230557 | A1* | 9/2012 | Calman | G06F 19/321 382/128 |
| 2014/0016842 | A1* | 1/2014 | Prigent | G06T 7/0012 382/128 |
| 2014/0358825 | A1* | 12/2014 | Phillipps | G06N 99/005 706/11 |
| 2014/0358828 | A1* | 12/2014 | Phillipps | G06N 99/005 706/12 |
| 2015/0045631 | A1* | 2/2015 | Ademola | A61B 5/6898 600/301 |
| 2015/0086104 | A1* | 3/2015 | Miyamoto | G06T 7/0012 382/133 |
| 2015/0099947 | A1* | 4/2015 | Qu | A61B 5/442 600/306 |
| 2015/0186518 | A1* | 7/2015 | Kusumoto | G06Q 30/0631 709/203 |
| 2016/0063312 | A1* | 3/2016 | Hara | A61B 5/0077 382/103 |
| 2016/0193108 | A1* | 7/2016 | Cho | A61N 2/00 600/9 |
| 2016/0256369 | A1* | 9/2016 | Dutton | A61K 8/342 |
| 2016/0331308 | A1* | 11/2016 | Zhou | A61B 5/4836 |
| 2016/0357578 | A1* | 12/2016 | Kim | G06F 9/4446 |
| 2017/0181963 | A1* | 6/2017 | Santhanam | A61K 8/342 |
| 2017/0220943 | A1* | 8/2017 | Duncan | G06N 5/04 |
| 2017/0245939 | A1* | 8/2017 | Kusumoto | G06Q 30/0631 |
| 2017/0246473 | A1* | 8/2017 | Marinkovich | A61N 5/0616 |
| 2017/0270593 | A1* | 9/2017 | Sherman | G06K 9/00268 |
| 2017/0270774 | A1* | 9/2017 | Fateh | A45D 40/0068 |
| 2018/0085048 | A1* | 3/2018 | Lee | A61B 5/442 |
| 2018/0276732 | A1* | 9/2018 | Pai | G06T 7/0012 |

* cited by examiner

METHOD FOR OBTAINING SKIN CARE INFORMATION, METHOD FOR SHARING SKIN CARE INFORMATION, AND ELECTRONIC APPARATUS THEREFOR

CROSS-REFERENCE TO RELATED APPLICATION

This application claims the priority benefit of Taiwan application serial no. 105116064, filed on May 24, 2016. The entirety of the above-mentioned patent application is hereby incorporated by reference herein and made a part of this specification.

BACKGROUND

Technical Field

The disclosure relates to a technique for sharing information regarding skin detection and skin care, and more particularly, relates to a method for obtaining skin care information, a method for sharing skin care information and an electronic apparatus therefor.

Description of Related Art

The traditional skin detection usually adopts a professional skin detecting apparatus to scan human skin in order to obtain its skin condition. Salesperson of the service provider can also recommend the corresponding care products according to the skin condition. However, it is difficult for the users to own such skin detecting apparatus. The reason is that, the skin detecting apparatus is usually expensive and extremely large. Also, the skin detecting apparatus requires installation of microscopes with different multiplying powers to scan skin, and thus the skin detecting apparatus can take a long time to operate since only a small portion of skin area can be scanned each time. Moreover, the users must be well-trained in order to determine the skin condition by using the skin detecting apparatus. Therefore, in the case where the users wish to know whether their own skin or skin condition are indeed improved at all times, the skin detecting apparatus may not satisfy such demand.

On the other hand, in order to maintain youth and beauty in a more efficient and time-saving manner, it is quite common that the users wish to learn care information regarding how others taking care of their own skin, how long it would take for the skin care, what sort of care product to be used, and the like. Nonetheless, reliability of the care information is hard to determine but can only be determined by the users themselves. Further, because each person may have skin, growing environment and diet very different from the others, reliability of the care information cannot be ensured simply by using one method. Accordingly, it has become one of most wanted product features for the users wishing to improve their own skin conditions as how to perform the skin detection, record the progress of skin care and share the care information with the others.

SUMMARY

The disclosure is directed to a method for obtaining skin care information and an electronic apparatus therefor, by which the user can obtain care information (e.g., care actions, used care products, etc.) shared by the other users as references to a facial skin care for the user.

On the other hand, the disclosure provides a method for sharing skin care information and an electronic apparatus therefor, by which the user can share a skin care history to the other users having the same skin condition by the electronic apparatus after achieving a skin-condition goal, so as to share personal tips for the facial skin care.

The method for obtaining care info illation of the disclosure is adapted to an electronic apparatus that includes an image capturing equipment. The method includes the following steps: obtaining face data of a current user from the image capturing equipment and analyzing the face data to obtain initial skin information; classifying the current user into one of a plurality of groups according to the initial skin information by a cloud database, wherein each of the groups includes a plurality of classified users; setting a predetermined time period and a skin-condition goal by the electronic apparatus; and obtaining a skin-achievement history corresponding to one of the classified users from the one of the groups containing the current user according to the initial skin information, the predetermined time period and the skin-condition goal by the electronic apparatus. The skin-achievement history is care information regarding the skin-condition goal achieved by the one of the classified users under circumstances of the approximate initial skin information and the approximate predetermined time period.

In an embodiment of the disclosure, the step of classifying the current user into the one of the groups includes: classifying the current user into the one of the groups according to the initial skin information and a plurality of classification criteria. The classification criteria may be one of gender, age, geographical location, race information and the predetermined time period of the current user, or a combination thereof.

In an embodiment of the disclosure, the method further includes: continuously recording current skin information and the care information of the current user within the predetermined time period and determining whether the skin-condition goal is achieved by comparing the initial skin information with the current skin information; and arranging the care information of the current user within the predetermined time period into a skin-achievement history corresponding to the current user when the skin-condition goal is achieved.

In an embodiment of the disclosure, the initial skin information or the current skin information includes a plurality of variable features analyzed from the face data. The variable features include one of wrinkles, facial lines, Erythema, acne, spots, pores, skin color and dark circle, or a combination thereof.

In an embodiment of the disclosure, the initial skin information or the current skin information further includes a plurality of skin parameters calculated according to the variable features. The skin parameters include one of clearness, texture, firmness, brightness and healthiness, or a combination thereof.

In an embodiment of the disclosure, the care information at least includes a care action and a used care product of the one of the classified users.

The method for sharing care information of the disclosure is adapted to an electronic apparatus that includes an image capturing equipment. The method includes the following steps: obtaining face data of a current user from the image capturing equipment and analyzing the face data to obtain current skin information as initial skin information; setting a predetermined time period and a skin-condition goal by the electronic apparatus; continuously recording the current skin information and care information of the current user within the predetermined time period and determining whether the skin-condition goal is achieved by comparing the initial skin information with the current skin information by the electronic apparatus; arranging the care information of the current user within the predetermined time period into a skin-achievement history corresponding to the current user when the skin-condition goal is achieved; and sharing the skin-achievement history corresponding to the current user to an another user who wishes to achieve the skin-condition goal under circumstances of the approximate initial skin information and the approximate predetermined time period.

An electronic apparatus of the disclosure includes an image capturing equipment, an input equipment and a network communication equipment. The image capturing equipment obtains face data of a current user. The processor is coupled to the image capturing equipment and the input equipment. The processor connects to a network via the network communication equipment. The processor analyzes the face data to obtain initial skin information, and classifies the current user into one of a plurality of groups according to the initial skin information by a cloud database in the network, where each of the groups includes a plurality of classified users. The input equipment receives a predetermined time period and a skin-condition goal set by the current user, and the processor obtains a skin-achievement history corresponding to one of the classified users from the one of the groups containing the current user according to the initial skin information, the predetermined time period and the skin-condition goal. The skin-achievement history is care information regarding the skin-condition goal achieved by the one of the classified users under circumstances of the approximate initial skin information and the approximate predetermined time period.

Based on the above, according to the embodiments of the disclosure, the image capturing equipment in the electronic apparatus is used to perform the skin detection for the user in order to obtain the initial skin information of the user, and the cloud database is used to classify users having the approximate environment, the approximate predetermined time period and the approximate skin-condition goal for improving the skin condition into the same group. If the skin-condition goal is achieved by the user within the predetermined time period, the electronic apparatus can then arrange the care information (e.g., the care action for skin, the used care products, etc.) of the user within the predetermined time period, and share the skin-achievement history to the other users having the same condition in the same group. As such, personal tips for the facial skin care may be shared. On the other hand, the user can also obtain the care information shared by the other users as references to the facial skin care for the current user.

To make the above features and advantages of the disclosure more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF THE EMBODIMENTS

Figure 1:
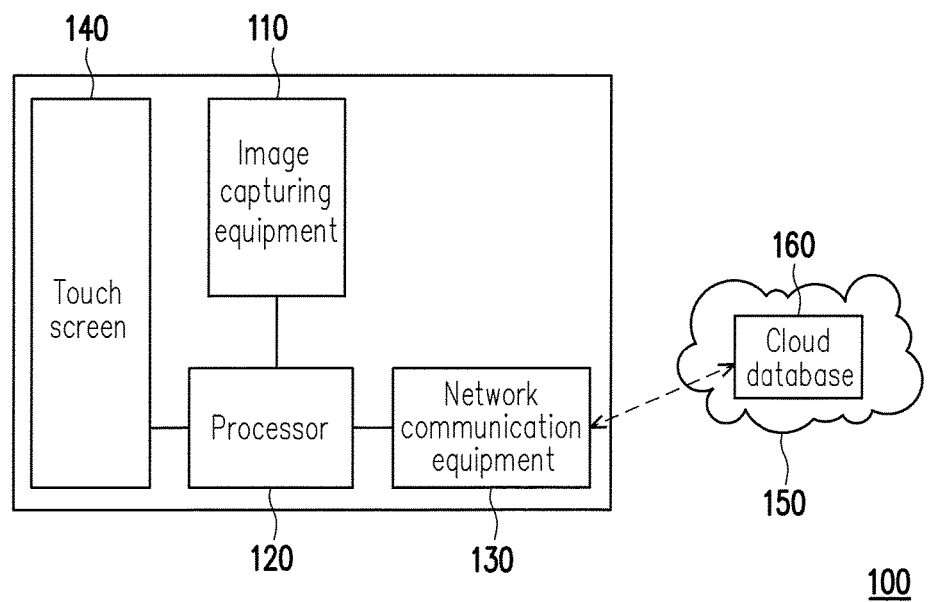
FIG. 1 is a schematic diagram of an electronic apparatus according to an embodiment of the disclosure.

It should be understood that the foregoing and other detailed descriptions, features, and effects are intended to be described more comprehensively by providing embodiments accompanied with drawings hereinafter. In the following embodiments, wording used to indicate directions, such as "up," "down," "front," "back," "left," and "right," merely refers to directions in the accompanying drawings. Therefore, the directional wording is used to illustrate rather than limit the disclosure. Moreover, the same or similar reference numerals represent the same or similar elements in the following embodiments.

FIG. 1 is a schematic diagram of an electronic apparatus 100 according to an embodiment of the disclosure. The electronic apparatus 100 includes an image capturing equipment 110, a processor 120, a network communication equipment 130, a display screen and an input equipment. The processor 120 is coupled to the image capturing equipment 110, the network communication equipment 130, the display screen and the input equipment. In the present embodiment of the disclosure, the electronic apparatus 100 may be an equipment installed on a dressing table, for example. In this case, the display screen of the electronic apparatus 100 may be installed behind a mirror of the dressing table to display text or image, as well as a skin-achievement history of the other users, through the mirror for viewing by the user.

In other embodiments, the electronic apparatus 100 may also be consumer electronic products (e.g., a smart phone, a tablet computer, etc.) or may be a portable mirror box formed in combination with a portable mirror. In the present embodiment, the display screen and the input equipment may be implemented by using a touch screen 140. In the present embodiment of the disclosure, a glass part disposed outside the touch screen 140 may be composed of the mirror to provide effectiveness of the mirror.

The image capturing equipment 110 may be a camera, which is configured to capture image in order to obtain face data of a current user. The processor 120 may be a central processing unit, an image processor or a special purpose processor. The processor 120 analyzes the face data obtained by the image capturing equipment 110 before performing steps in the subsequent process. The processor 120 connects to a network 150 via the network communication equipment 130. The network communication equipment 130 may be a networking chip or a network card supporting one or more network communication protocols (e.g., a wireless network protocol, a bluetooth protocol, etc.). In the present embodiment, the network 150 includes a cloud database 160. The cloud database 160 can include personal information (e.g., age of the user, geographical location, etc.) of various users and the skin-achievement history for the facial skin care. Also, the cloud database 160 can classify these users into different groups according to a plurality of classification criteria. Details regarding how to classify the users according to the classification criteria will be provided later in the following description.

Steps in the method for obtaining care information and the method for sharing care method in accordance with the embodiments of the disclosure may be implemented by using hardware or firmware chips in the electronic apparatus, and may also be implemented by using software or APP executed by the processor 120 in the electronic apparatus 100.

Figure 2:
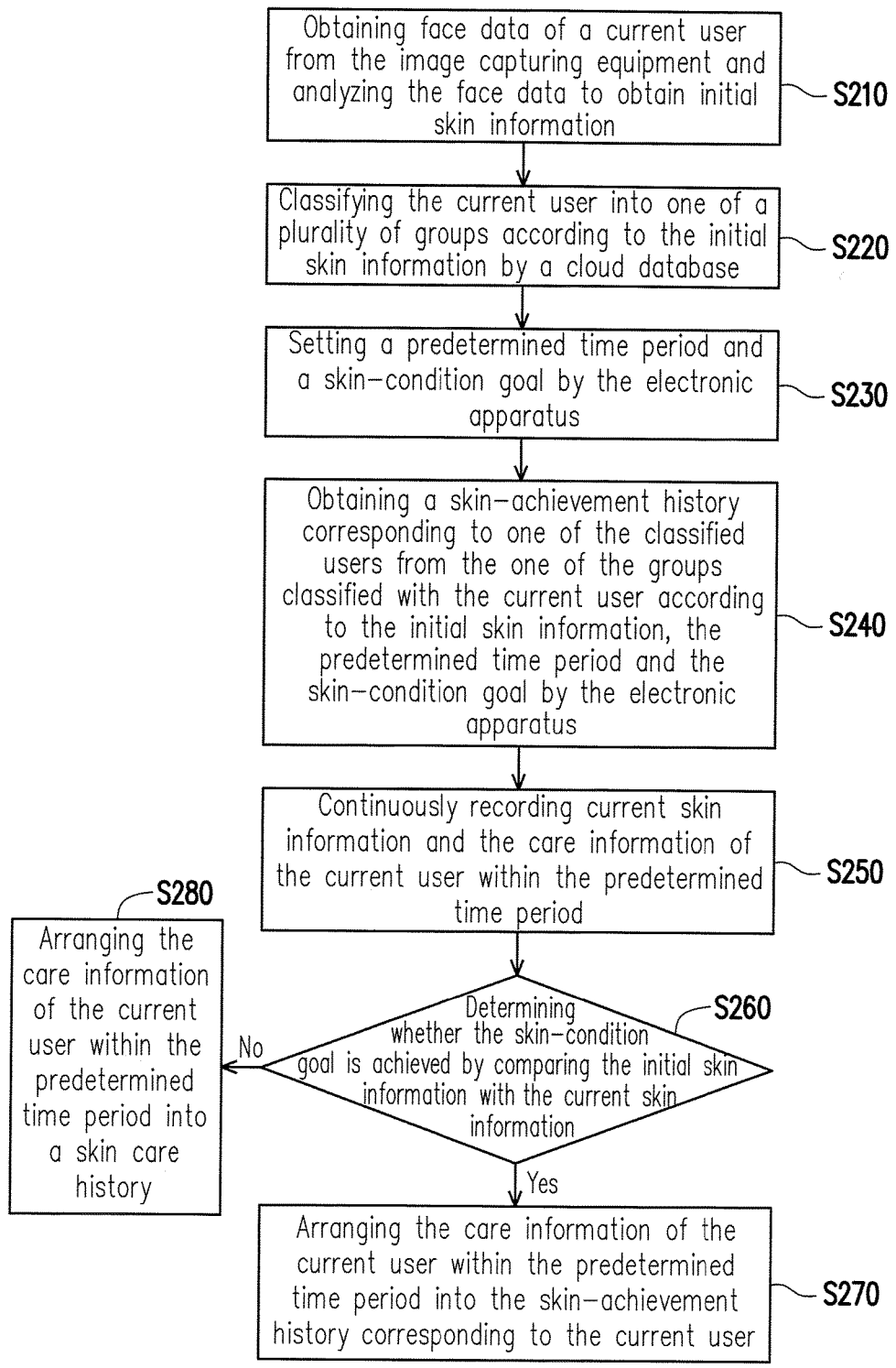
FIG. 2 is a flowchart of a method for obtaining care information according to an embodiment of the disclosure.

FIG. 2 is a flowchart of a method for obtaining care information according to an embodiment of the disclosure. In the present embodiment of the disclosure, the method for obtaining care information is adapted to the electronic apparatus 100 which includes the image capturing equipment 110, as shown in FIG. 1. Each step in the flowchart of FIG. 2 is described with reference to each element of the electronic apparatus 100 in FIG. 1. In step S210, the processor 120 obtains face data of a current user from the image capturing equipment 110 and the processor 120 analyzes the face data of the current user to obtain initial skin information. In the present embodiment, the image capturing equipment 110 may require a capturing capability for higher image resolution, or may take multiple shots to obtain more preferable images. The reason is that, to detect the skin condition on human face in detail, the images must have higher resolution, the number of effective pixels greater than a preset number (e.g., 4M pixels) for the entire face and non-blur images. Otherwise, the subsequent recognition of the face data cannot be performed on blur images.

Figure 3:
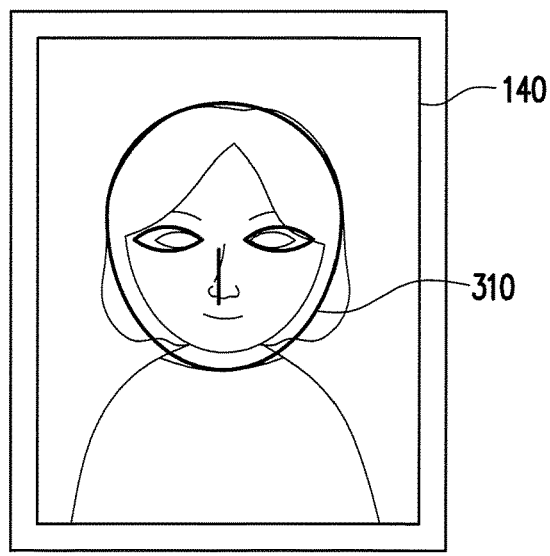
FIG. 3 is a schematic diagram of the touch screen and a face markup according to an embodiment of the disclosure.

Here, detailed process in step S210 will be described in detail below. First of all, the processor 120 obtains the face data of the current user from the image capturing equipment 110. FIG. 3 is a schematic diagram of the touch screen 140 and a face markup 310 according to an embodiment of the disclosure. Referring to FIG. 3, when it is intended to obtain the face data of the current user, one face markup 310 may be presented on the display screen (e.g., the touch screen 140) while presenting an image currently captured by the image capturing equipment 110 on the touch screen 140. In other words, the main purpose the face markup 310 of the present embodiment is to mark up locations of face portions (including a facial contour, eyes, a nose bridge, etc.) of the current user that the electronic apparatus 100 intends to obtain the image of user face in the face markup 310 on the touch screen 140. Those applying the present embodiment may also implement the above by adopting the face markup of other types, such as a face markup that only includes the facial contour or only includes locations of the eyes. In this way, the user is able to self-align the face portions to the face markup 310 so the processor 120 can be more accurate when obtaining the face data and determining the initial skin information in the subsequent process. If the current user does not align the face portions in a manner of straightly facing the image capturing equipment 110 due to photographic posture (e.g., when the face portions of the current user being overly tilted to a lateral side, an area below the lip among the face portions being too small, etc.), a face recognition cannot be performed since an area including the face portions may not be completely captured.

Referring back to FIG. 1 and step S210 of FIG. 2, after obtaining the face data of the current user, the processor 120 analyzes the face data of the current user to obtain the initial skin information. Description regarding how the processor 120 analyzes the face data to obtain the skin information (e.g., the initial skin information and current skin information described below) is provided as follows. In the present embodiment, the skin information may be a severity level of a plurality of variable features related to skin and obtained by analyzing different regions in the face image of the current user, where the variable features may be used to calculate each of skin parameters related to skin. These variable features are, for example, wrinkles, facial lines, Erythema, acne, spots, pores, skin color, dark circle and the like. The processor 120 in the electronic apparatus 100 may obtain the variable features according to a specific determination reference and the severity level, and calculate the face parameters according to the variable features.

Figure 4:
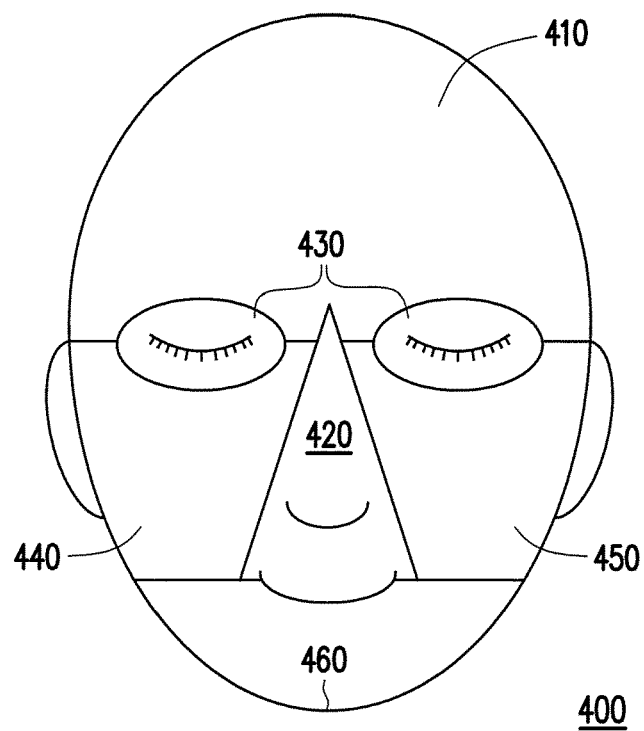
FIG. 4 is a schematic diagram of each of face portions of the face data according to an embodiment of the disclosure.

FIG. 4 is a schematic diagram of each of face portions 410 to 460 of the face data according to an embodiment of the disclosure. Referring to FIG. 4, FIG. 4 is face data 400 of the current user obtained by the processor 120, and the face data 400 is divided into a plurality of face portions 410 to 460 by using a face precognition technology. These face portions 410 to 460 include a forehead portion 410, a nose portion 420, an eyes portion 430, a right-face portion 440, a left-face portion 450 and a chin portion 460. The variable features described above may have different feature definitions due to different portions in which they appear or their severity level, and the variable features are explained one by one with reference to FIG. 4 in the present embodiment. In the present embodiment, the severity level of the variable features is further divided into level 1 (least severe) to level 5 (most severe), and areas of the variable features are referred as fractions for calculating their area percentages relative to the entire face. Those applying the present embodiment should also understand that definitions of these variable features may also be adjusted based on demands rather than limited by the embodiments of the present application.

The term so-called "wrinkles" refers to a linear crease in the face data 400 of the entire face that is deeper and longer, and may appear in each of the face portions 410 to 460. In the present embodiment, maximum values, average values and minimum values of depth and length of "wrinkles" may be obtained through the cloud database 160 or user face data from other sources, and those values may be used to calculate the number of wrinkles in the face data 400 and an area percentage of wrinkles relative to the entire face. Further, in the present embodiment, wrinkles are marked up in a labeling manner in the face data 400 as references for the user. The term so-called "facial lines" refers to a linear crease in the face data 400 of the entire face that is shallower and shorter, and may appear in each of the face portions 410 to 460. In the present embodiment, maximum values, average values and minimum values of depth and length of "facial lines" may be obtained through the cloud database 160 or user face data from other sources, and those values may be used to calculate the number of facial lines in the face data and an area percentage of facial lines relative to the entire face. Further, in the present embodiment, facial lines are marked up in a labeling manner in the face data 400 as references for the user.

The term so-called "Erythema" refers to a plaque in the face data 400 of the entire face that is reddish compared to user's skin color and has a larger area, and may appear in each of the face portions 410 to 460. An area percentage of Erythema relative to the entire face may be obtained through a face image recognition technology. The term so-called "acne" refers to a plaque in the face data 400 of the entire face that is reddish compared to user's skin color and has a smaller area, and may appear in each of the face portions 410 to 460. The number of acne in the face data 400 may be obtained through the face image recognition technology, and used to determine the severity level according to said number. The term so-called "spots" refers to a plaque or a spot in the face data 400 of the entire face that is darker compared to user's skin color, and may appear in each of the face portions 410 to 460. The number of spots in the face data 400 and an area percentage of spots relative to the entire face may be obtained through the face image recognition technology, and used to determine the severity level according to said number and said area percentage. The term so-called "pores" refers to a pore and an opening on a skin surface in the right-face portion 440, the left-face portion 450 and the nose portion 420. The number of pores in the face data 400 and area percentages of pores relative to the right-face portion 440, the left-face portion 450 and the nose portion 420 may be obtained through the face image recognition technology, and used to determine the severity level according to said number and said area percentages.

The term so-called "skin color" refers to an average skin color of skin itself in the face data 400 of the entire face. The average color herein may not include a skin color of dark circle and skin colors at places where acne and spots appear. The term so-called "dark circle" refers to a skin color at places below the eyes portion 430.

The variable features belong to absolute values in the face data 400 but are still slightly different from specific skin parameters commonly used in the field of the facial skin care. Therefore, in the present embodiment, the processor 120 of FIG. 1 may calculate the skin parameters according to the variable features. These skin parameters are the determination criteria commonly used in the field of the facial skin care. The skin parameters are, for example, clearness, texture, firmness, brightness, healthiness, and the like. In the present embodiment, the skin parameters are based on two face images of the user being taken. For example, a skin progress level between the two face images may be calculated by, for example, comparing the initial skin information with the current skin information. As such, these skin parameters may be expressed in percentages (%). "Clearness" of skin may be obtained by calculating a white level of the entire face, a reduced number or a reduced area of face pores (e.g., spots, Erythema, acne, pores) on the face as well as a color-fading level of dark cycle. "Texture" of skin is mainly obtained by calculating a coverage area of facial lines, and may also be obtained by calculating the number of and a coverage area of pores as a secondary option. "Firmness" of skin is obtained by calculating the number and the area of pores. "Brightness" of skin is mainly obtained by calculating a brightness level of the entire face as a major variable feature. "Healthiness" of skin is mainly obtained by calculating the number of Erythema and a coverage area of Erythema as major variable features.

Referring to FIG. 1 and FIG. 2, the method proceeds to step S220 after step S210 is completed. In step S220, the processor 120 classifies the current user into one of a plurality of groups according to the initial skin information by the cloud database 160 in the network 150. In the present embodiment, each of the groups in the cloud database 160 includes a plurality of classified users. The purpose of step S220 aims to classify users with the same geographical location, the same environment, similar race or even similar diet into the same group, so that the users in the same group are able to share skin care histories and experiences with one another.

In the present embodiment of the disclosure, the current user is classified into the corresponding group mainly according to the initial skin information so the users with identical or approximate skin information may be classified into the same group. In some embodiments in a consistent with the scope of the disclosure, other than classifying the users according to the initial skin information, the processor 120 may also classify the current user into one of the groups according to a plurality of classification criteria. The classification criteria of the present embodiments of the disclosure may be implemented by various ways, and these each of the classification criteria may be implemented by classifying the current user. The classification criteria may be, classification criteria mainly based on the user, such as one or more of gender, age, geographic position and race information of the current user, or a combination thereof. The classification criteria may also be: a predetermined time period and a skin-condition goal set by the current user. Detailed descriptions regarding "predetermined time period" and "skin-condition goal" will be provided in following embodiments.

The first classification criterion is gender of the user. Because the skin conditions of the male user and the female user are very different, the user with different gender may have to be classified first. The second classification criterion may be age of the user. The skin conditions and the skin care histories of users of age 20 to 25 years and users of age 26 to 30 are also very different. The third classification criterion may be a relationship between geographic locations (e.g., the users are classified according to countries or geographical regions where the users are located). The geographical regions may be classified according to seven continents on Earth (e.g., Asia, North America, etc.). This classification criterion aims to classify the user information with approximate geographical environment into the same group. The fourth classification criterion may be "race". The term so-called "race" aims to obtain a race type of the user so the user may be classified into a group in which the users have the race type of common features in physical patterns or genetic characteristics. During the classification with "race", the users may self-select the "race" type of their own based on objective conditions such as appearance features (e.g., hair color, skin color and facial bone structure), gene, and the like. In actual implementations, the race type of the user may be determined by the image capturing equipment on the electronic apparatus through image recognition technology, or may be determined by the language being selected. The "race" type may be Congoid race (i.e., black people), Caucasian race (i.e., white people), Mongoloid race (i.e., yellow people), Australoid race (i.e., brown people) and Capoid race (an independent race different from the traditional black people). It is possible that the users may have trouble selecting the "race" of their own as the classification criterion. In that case, "language" may be used to replace "race" as the classification criterion since most of people with the same race speak similar languages. Those applying the present embodiment may appropriately adjust whether or not to use the classification criteria or add other classification criteria according to the amount of user data in the database or differences in data content, rather than limited by the foregoing embodiments.

In step S230, the current user can set a predetermined time period and a skin-condition goal for the desired improvement by using the input equipment (e.g., the touch screen 140) in the electronic apparatus 100. "Predetermined time period" and "skin-condition goal" may be set by the user or may be recommended by the electronic apparatus 100 through the cloud database 160. "Predetermined time period" may be set to, for example, one week, one month, three months, six months, one year or two years; "Skin-condition goal" may be set to, for example, a desired percentage of clearness to be improved, a desired reduction on the severity level of wrinkles, and the like.

In step S240, after receiving the "predetermined time period" and the "skin-condition goal", the electronic apparatus 100 obtains a skin-achievement history corresponding to one of the classified users from one of the groups containing the current user according to the initial skin information, the predetermined time period and the skin-condition goal. The skin-achievement history is care information regarding the skin-condition goal achieved by the one of the classified users under circumstances of the approximate initial skin information and the approximate predetermined time period. In other words, the electronic apparatus 100 searches the group containing the current user in the cloud database 160 for the skin-achievement history having the identical or approximate initial skin information, having the identical or approximate predetermined time period, having the identical or approximate skin-condition goal and already being achieved by the other users of the same group in step S240, so the skin-achievement history can serve as references for the current user. The care information at least includes at least one care action and at least one or more used care products of the classified users. Accordingly, with use of the electronic apparatus 100, the current user is able to obtain the care information shared by the other users as references to the facial skin care for the current user. On the other hand, the electronic apparatus 100 may also provide purchase information of the care products in the care information or products with identical or similar effect of said care products, so as to further extend functionality of the electronic apparatus 100.

It should be noted that, the users in the same group or the same level can only be referred to as having approximate skin information and conditions since the skin information of each user is classified or identified by ways of dividing the skin condition into different types or levels (e.g., the skin condition may be divided into levels 1 to 10). Therefore, when the users are classified into different groups according to the initial skin information, the skin conditions of users in the same group are approximate.

If the current user wishes to conduct the facial skin care according to the care information in the skin-achievement history after obtaining the skin-achievement history, in step S250, the processor 120 of the electronic apparatus 100 continuously records the current skin information of the current user and the care information of the current user (e.g., the used care product, the skin care action, etc.) within the predetermined time period. Then, in step S260, the processor 120 determines whether the skin-condition goal set by the current user is achieved by comparing the initial skin information in an initial detection with the current skin information.

When the skin-condition goal set by the current user is achieved with the predetermined time period, the method proceeds from step S260 to step S270, in which the processor 120 arranges the care information of the current user within the predetermined time period into the skin-achievement history corresponding to the current user. Later, the processor 120 can inquire the current user whether to upload the skin-achievement history to the cloud database 160. By doing so, the skin-achievement history may be shared to an another user who wishes to achieve the skin-achievement history under circumstances of the approximate initial skin information and the approximate predetermined time period, where said another user and the current user belong to the same group. On the other hand, when the skin-condition goal set by the current user is not achieved within the predetermined time period, the method proceeds from step S260 to step S280. In step S280, the processor 120 may also arrange the care information of the current user within the predetermined time period into a skin care history, and the skin care history may be shared to the other users, the service provider or even dermatologists so they confirm whether this skin care history can indeed improve the facial skin. Moreover, it is likely that dermatologists may provide suggestions for improvement regarding the skin care history to further improve the care information and the flow.

Figure 5:
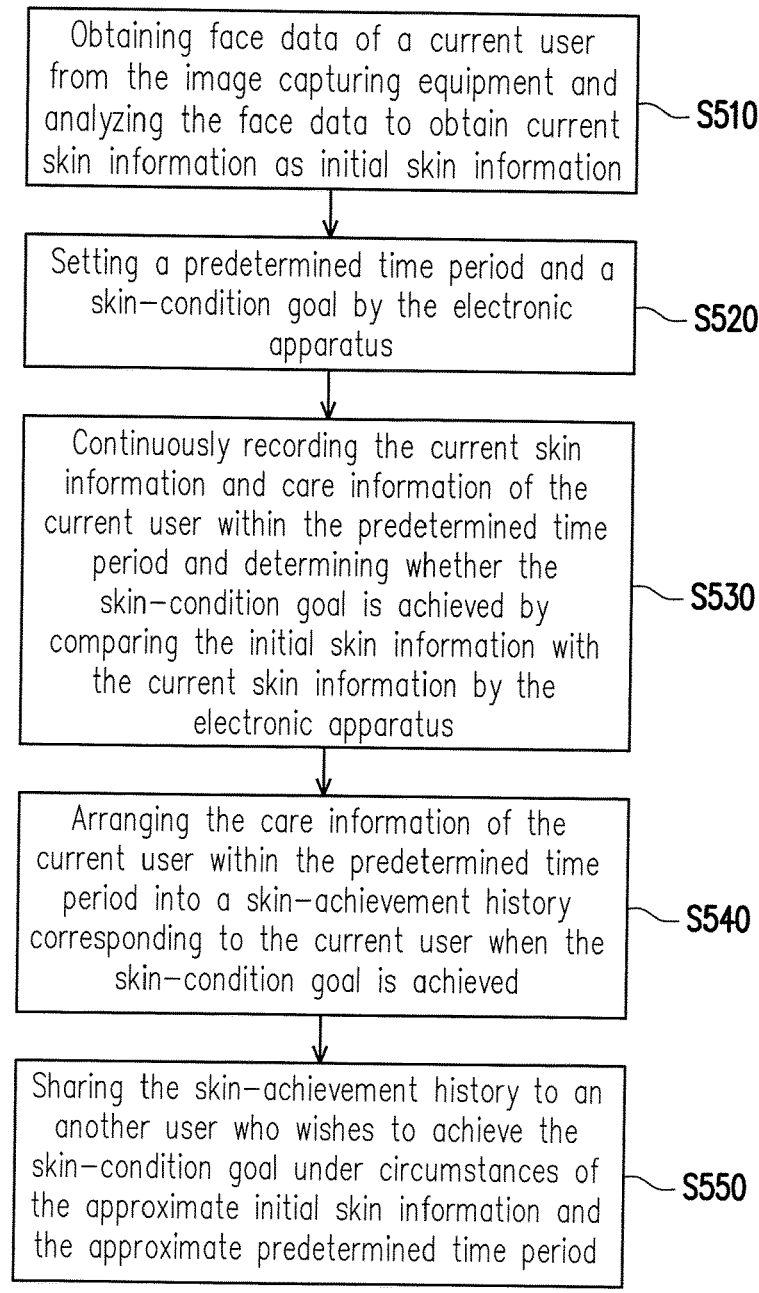
FIG. 5 is a flowchart of a method for sharing care information according to an embodiment of the disclosure.

FIG. 5 is a flowchart of a method for sharing care information according to an embodiment of the disclosure. In the present embodiment of the disclosure, the method for sharing care information is adapted to the electronic apparatus 100 which includes the image capturing equipment 110, as shown in FIG. 1. Each step in the flowchart of FIG. 5 is described with reference to each element of the electronic apparatus 100 in FIG. 1. In step S510, the processor 120 obtains face data of current user from the image capturing equipment 110, and the processor 120 analyzes the face data to obtain current skin information as initial skin information. In step S520, the processor 120 sets a predetermined time period and a skin-condition goal by the input equipment (e.g., the touch screen 140) in the electronic apparatus 100. In step S530, the current user may use various elements in the electronic apparatus 100 to continuous record the current skin information and care information of the current user within the predetermined time period and determines whether the skin-condition goal is achieved by comparing the initial skin information with the current skin information. In step S540, when determining that the skin-condition goal is achieved within the predetermined time period, the processor 120 arranges the care information of the current user within the predetermined time period into a skin-achievement history corresponding to the current user. In step S550, the processor 120 can share the skin-achievement history corresponding to the current user by the network communication equipment 130 through the cloud database 160 in the network 150 to an another user who wishes to achieve the same skin-condition goal under circumstances of the approximate initial skin information and the approximate predetermined time period. In the present embodiment, said current user and said another user should be classified into the same group. Detailed steps of the above may refer to the foregoing embodiment.

In summary, according to the embodiments of the disclosure, the image capturing equipment in the electronic apparatus is used to perform the skin detection for the user in order to obtain the initial skin information of the user, and classifies users having the approximate environment, the approximate predetermined time period and the approximate skin-condition goal for improving the skin condition into the same group. If the skin-condition goal is achieved by the user within the predetermined time period, the electronic apparatus can then arrange the care information (e.g., the care action for skin, the used care products, etc.) of the user within the predetermined time period, and share the skin-achievement history to the other users having the same condition in the same group. As such, personal tips for the facial skin care may be shared. On the other hand, the user can also obtain the care information shared by the other users as references to the facial skin care for the current user.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:
1. A method for obtaining care information, adapted to an electronic apparatus including an image capturing equipment, a processor, and an input equipment, the method comprising:

capturing an image of a current user by using the image capturing equipment to generate face data;

obtaining the face data from the image capturing equipment by the processor and analyzing the face data by the processor to obtain initial skin information, wherein the initial skin information comprises a plurality of skin parameters calculated according to variable features comprising an unwanted facial feature analyzed from the face data through image recognition, and wherein the skin parameters are numeric and calculated based on a severity level of the unwanted facial feature or an area percentage of the unwanted facial feature relative to an entire face;

classifying the current user into one of a plurality of groups by the processor according to the initial skin information and at least one of a plurality of classification criteria associated with demographic attributes by using a cloud database, wherein each of the groups comprises a plurality of classified users;

receiving a desired predetermined time period and a skin-condition goal for a desired skin improvement inputted by the current user through the input equipment by the processor, wherein the skin condition goal is a desired reduction on the severity level of the unwanted facial feature or a desired percentage of the unwanted facial feature relative to the entire face to be improved, and wherein the desired predetermined time period is a total treatment time needed for achieving the skin-condition goal;

obtaining a skin-achievement history corresponding to one of the classified users from the one of the groups containing the current user by the processor according to the initial skin information, the desired predetermined time period and the skin-condition goal for the desired skin improvement, wherein the skin-achievement history is care information regarding the skin-condition goal achieved by the one of the classified users under circumstances of approximate initial skin information approximated to the initial skin information and approximate predetermined time period approximated to the desired predetermined time period, wherein the care information comprises care actions and used care products of the one of the classified users; and implementing a treatment for achieving the skin-condition goal using the care information regarding the skin-condition goal achieved by the one of the classified users under the circumstances of the approximate initial skin information approximated to the initial skin information and the approximate predetermined time period approximated to the desired predetermined time period.

2. The method for obtaining care information according to claim 1,
wherein the at least one of the plurality of classification criteria comprises one of gender, age, geographical location, and racial information of the current user, or a combination thereof.

3. The method for obtaining care information according to claim 1, further comprising:
continuously recording current skin information and care information of the current user within the desired predetermined time period and determining whether the skin-condition goal is achieved by comparing the initial skin information with the current skin information; and arranging the care information of the current user within the desired predetermined time period into a skin-achievement history corresponding to the current user when the skin-condition goal is achieved.

4. The method for obtaining care information according to claim 3, wherein the at least one of the plurality of variable features comprising comprises one of wrinkles, facial lines, Erythema, acne, spots, pores, skin color and dark circle, or a combination thereof.

5. The method for obtaining care information according to claim 4,
wherein the at least one of the plurality of skin parameters comprises one of clearness, texture, firmness, brightness and healthiness, or a combination thereof.

6. A method for sharing care information, adapted to an electronic apparatus including an image capturing equipment, a processor, and an input equipment, the method comprising:

capturing an image of a current user by using the image capturing equipment to generate face data;

obtaining the face data from the image capturing equipment by the processor and analyzing the face data by the processor to obtain initial skin information, wherein the initial skin information comprises a plurality of skin parameters calculated according to variable features comprising an unwanted facial feature analyzed from the face data through image recognition, and wherein the skin parameters are numeric and calculated based on a severity level of the unwanted facial feature or an area percentage of the unwanted facial feature relative to an entire face;

classifying the current user into one of a plurality of groups by the processor according to the initial skin information and at least one of a plurality of classification criteria associated with demographic attributes by using a cloud database, wherein each of the groups comprises a plurality of classified users;

receiving a desired predetermined time period and a skin-condition goal for a desired skin improvement inputted by the current user through the input equipment by the processor, wherein the skin condition goal is a desired reduction on the severity level of the unwanted facial feature or a desired percentage of the unwanted facial feature relative to the entire face to be improved, and wherein the desired predetermined time period is a total treatment time needed for achieving the skin-condition goal;

obtaining a skin-achievement history corresponding to one of the classified users from the one of the groups containing the current user by the processor according to the initial skin information, the desired predetermined time period and the skin-condition goal for the desired skin improvement, wherein the skin-achievement history is care information regarding the skin-condition goal achieved by the one of the classified users under circumstances of approximate initial skin information approximated to the initial skin information and approximate predetermined time period approximated to the desired predetermined time period, wherein the care information comprises care actions and used care products of the one of the classified users;

implementing a treatment for achieving the skin-condition goal using the care information regarding the skin-condition goal achieved by the one of the classified users under the circumstances of the approximate initial skin information approximated to the initial skin information and the approximate predetermined time period approximated to the desired predetermined time period;

continuously recording the current skin information and care information of the current user within the desired predetermined time period and determining whether the skin-condition goal for the desired skin improvement is achieved by comparing the initial skin information with the current skin information by the processor;

arranging the care information of the current user within the desired predetermined time period into a skin-achievement history corresponding to the current user by the processor when the skin-condition goal is achieved; and sharing the skin-achievement history to an another user who wishes to achieve the skin-condition goal under circumstances of the approximate initial skin information approximated to the initial skin information and the approximate desired-predetermined time period approximated to the desired predetermined time period and who is classified into a same group as the current user by the processor.

7. The method for sharing care information according to claim 6, wherein the at least one of the plurality of classification criteria comprises one of gender, age, geographical location, and racial information of the current user, or a combination thereof.

8. An electronic apparatus, comprising:

an image capturing equipment, capturing an image of a current user to generate face data;

a processor, coupled to the image capturing equipment;

an input equipment, coupled to the processor; and a network communication equipment, wherein the processor connects to a network via the network communication equipment, wherein the processor is configured to:

obtain the face data from the image capturing equipment and analyze the face data to obtain initial skin information, wherein the initial skin information comprises a plurality of skin parameters calculated according to variable features comprising an unwanted facial feature analyzed from the face data through image recognition, and wherein the skin parameters are numeric and calculated based on a severity level of the unwanted facial feature or an area percentage of the unwanted facial feature relative to an entire face;

classify the current user into one of a plurality of groups according to the initial skin information and at least one of a plurality of classification criteria associated with demographic attributes by using a cloud database, wherein each of the groups comprises a plurality of classified users;

receive a desired predetermined time period and a skin-condition goal for a desired skin improvement inputted by the current user through the input equipment, wherein the skin condition goal is a desired reduction on the severity level of the unwanted facial feature or a desired percentage of the unwanted facial feature relative to the entire face to be improved, and wherein the desired predetermined time period is a total treatment time needed for achieving the skin-condition goal;

obtain a skin-achievement history corresponding to one of the classified users from the one of the groups containing the current user according to the initial skin information, the desired predetermined time period and the skin-condition goal for the desired skin improvement, wherein the skin-achievement history is care information regarding the skin-condition goal achieved by the one of the classified users under circumstances of approximate initial skin information approximated to the initial skin information and approximate predetermined time period approximated to the desired predetermined time period, wherein the care information comprises care actions and used care products of the one of the classified users; and direct the user to implement a treatment for achieving the skin-condition goal using the care information regarding the skin-condition goal achieved by the one of the classified users under the circumstances of the approximate initial skin information approximated to the initial skin information and the approximate predetermined time period approximated to the desired predetermined time period.

9. The electronic apparatus according to claim 8, wherein the at least one of the plurality of classification criteria comprises one of gender, age, geographical location, racial information and the predetermined time period of the current user, or a combination thereof.

10. The electronic apparatus according to claim 8, wherein the processor continuously records current skin information and care information of the current user within the desired predetermined time period and determines whether the skin-condition goal is achieved by comparing the initial skin information with the current skin information, and the processor arranges the care information of the current user within the desired predetermined time period into a skin-achievement history corresponding to the current user and uploads the skin-achievement history corresponding to the current user to the cloud database when the skin-condition goal is achieved.

11. The electronic apparatus according to claim 10, wherein the at least one of the plurality of variable features comprises one of wrinkles, facial lines, Erythema, acne, spots, pores, skin color and dark circle, or a combination thereof.

12. The electronic apparatus according to claim 11, wherein the input equipment is a touch screen.

13. The electronic apparatus according to claim 8, wherein the at least one of the plurality of skin parameters comprises one of clearness, texture, firmness, brightness and healthiness, or a combination thereof.

14. The electronic apparatus according to claim 8, further comprising: a display screen, configured to display the skin-achievement history.

* * * * *